United States Patent [19]

Kreh et al.

[11] Patent Number: 4,670,108

[45] Date of Patent: Jun. 2, 1987

[54] OXIDATION OF ORGANIC COMPOUNDS USING CERIC METHANESULFONATE IN AN AQUEOUS ORGANIC SOLUTION

[75] Inventors: Robert P. Kreh, Jessup; Robert M. Spotnitz, Catonsville, both of Md.

[73] Assignee: W. R. Grace & Co., New York, N.Y.

[21] Appl. No.: 917,442

[22] Filed: Oct. 10, 1986

[51] Int. Cl.$^4$ .............................................. C25B 3/02
[52] U.S. Cl. ...................... 204/59 R; 204/78; 260/385; 260/396 R; 568/309; 568/426
[58] Field of Search ............... 204/59 R, 78; 568/309, 568/426; 260/385, 369 R

[56] References Cited

U.S. PATENT DOCUMENTS

| | | | |
|---|---|---|---|
| 808,095 | 12/1905 | Lang. | |
| 3,413,203 | 11/1968 | MacLean | 204/79 |
| 3,486,992 | 12/1969 | Frye | 204/86 |
| 3,873,580 | 3/1975 | Rennie | 260/396 R |
| 4,212,710 | 7/1980 | Halter et al. | 204/78 |
| 4,212,711 | 7/1980 | Halter et al. | 204/78 |
| 4,312,721 | 1/1982 | Oehr | 204/78 |
| 4,313,804 | 2/1982 | Oehr | 204/93 |
| 4,354,904 | 10/1982 | Malloy et al. | 204/59 R |
| 4,371,431 | 2/1983 | Switzer et al. | 204/79 R |
| 4,387,007 | 6/1983 | Seiler | 204/59 R |
| 4,482,438 | 11/1984 | Ballard et al. | 204/78 |
| 4,530,745 | 7/1985 | Komatsu et al. | 204/130 |
| 4,536,337 | 8/1985 | Komatsu et al. | 260/396 R |
| 4,560,804 | 12/1985 | Yeh et al. | 568/408 |
| 4,582,942 | 4/1986 | Comninellis et al. | 204/59 R |

FOREIGN PATENT DOCUMENTS

| | | | |
|---|---|---|---|
| 899856 | 5/1972 | Canada | 204/55 |
| 1132996 | 10/1982 | Canada | 260/396 |

OTHER PUBLICATIONS

J. Org. Chem (1983) vol. 48, pp. 1487–1491, by M. Marrocco et al.

Prospects for the Indirect Electrolytic Oxidation of Organics, by Ibl et al., Electro-Organic Synthesis Technology, No. 185, vol. 75 (1979) pp. 45–50.

Performance of Two-Phase Electrolyte Electrolysis, by H. Feess et al., Techniques of Chemistry, vol. V Part III, Ed. by N. L. Weinberg et al, pp. 104–176.

*Primary Examiner*—Arthur P. Demers
*Attorney, Agent, or Firm*—Howard J. Troffkin

[57] ABSTRACT

A process for oxidizing aromatic and alkyl substituted aromatic compounds to carbonyl containing compounds by contacting an aromatic or alkyl aromatic compound with ceric methanesulfonate in an aqueous, weakly acidic solution containing an organic cosolvent which has at least 2 percent solubility in water under reaction conditions and is substantially inert with respect to the acidic, oxidizing conditions.

33 Claims, No Drawings

OXIDATION OF ORGANIC COMPOUNDS USING CERIC METHANESULFONATE IN AN AQUEOUS ORGANIC SOLUTION

BACKGROUND OF THE INVENTION

The present invention is directed to an improved electrochemical oxidation process for forming quinones and aromatic aldehydes or ketones from corresponding aromatic and alkyl aromatic compounds in good yields and high selectivity. More specifically, the invention described and claimed herein requires the use of an aqueous-organic cosolvent system having low concentrations of methanesulfonic acid therein and high concentrations of ceric methanesulfonate dispersed therein.

The quinones obtainable by the present process have a wide variety of known utility. For example, quinones, such as naphthoquinone, are known intermediates to dyes and are additives in the paper making industry. The aldehydes, such as benzaldehyde, tolualdehyde and the like, and ketones, such as p-methylacetophenone, are known intermediates used in forming fragrance components useful in perfumes and colognes. Certain aldehydes and ketones have been used in forming pharmaceuticals.

The products achieved by the present invention have been previously formed by a variety of processes which may be generally classified as chemical or electrochemical. For example, aromatic aldehydes have been chemically formed by air oxidation conducted in an oxygen enriched environment at high temperatures and pressure in the presence of a transition metal catalyst or by using known chemical oxidizing agents which are not regenerable. Oxidation has also been achieved by direct electrochemical oxidation of aromatic compounds in the presence of dilute acid electrolytic solutions as described in U.S. Pat. Nos. 4,298,438 and 4,354,904 and by indirect electrochemical oxidation in which the oxidant is electrolytically generated and, in turn, used to oxidize the aromatic compound.

Compounds which are known to be capable of acting as an indirect oxidant include transition metal salts, particularly the metals of cobalt, chromium, manganese, iron, lead, silver and cerium. Because regeneration of the spent metal to its higher oxidation state is not always highly effective and/or other insoluble salts, such as oxides, etc., are formed, those skilled in this art tend to use the salts of chromium, manganese, cobalt, iron or lead as these salts are less expensive and replacement of spent materials does not greatly detract from the economics of the process. However, each of these metal ion oxidants have certain properties which cause them to make the oxidation process ineffective. For example, chromium ions give poor selectivity towards the desired products, cerium and manganese salts are believed to have low solubility of the oxidized and/or reduced ions in acidic solutions causing reduced activity or separation problems, the higher oxidation states of silver, cobalt and lead ions are not very stable and, in the case of iron, is not very reactive. Indirect electrochemical oxidation has been further complicated by the properties of the anion specie present. For example, certain anions (e.g., chloride, nitrate, perchlorate) are highly reactive with the organic substrate producing by-products or conditions which preclude their use on a commercial scale. Other less reactive anions (e.g., sulfate, acetate, fluoride, boron fluoride, silicon fluoride) generally form salts of low solubility, inhibit the rate of reaction of the oxidant with the organic substrate and/or inhibit the ability of the spent oxidant to be regenerated. In addition, certain organic acid salts (e.g., benzenesulfonate) have been found to be insufficiently stable to be useful in an indirect oxidation process.

Ceric ion is a well known oxidizing agent in organic chemistry. It has the potential of presenting an excellent one electron oxidant but has not been previously used extensively or on an industrial scale because of the inability of both the ceric and cerous ions to be maintained in solution at high concentrations causing its use to be limited to slurries or very low concentrations with concomitant slow reactivity. The cerium salts are prohibitively expensive and, therefore, must be capable of being stable, achieving good reaction rates, reacting with the organic substrate cleanly and easily regenerating to its higher valence state. In addition, the cerous ion must be highly soluble to be capable of being regenerated to the ceric ion under conditions of high current efficiency in the anodic portion of the electrochemical cell. However, conditions preferred for best utilization of the ceric ion have previously been believed as being counterproductive to achieving proper conditions for cerous salt utilization. Therefore, it has heretofore been believed necessary to use the cerium salt at very low concentrations and under a very narrow set of conditions including those which could not demonstrate the potential necessary to provide an effective industrially suitable process.

Canadian Pat. No. 1,132.996, to Oehr describes a process for oxidizing naphthalene to naphthaquinone using ceric sulfate in dilute sulfuric acid. Both cerous sulfate and ceric sulfate are known to have low solubility in dilute acid [Solubilities of Inorganic and Organic Compounds, Vol. 3, Part I, Ed. by H. L. Silcock (1974)] and the solubility decreases with increasing acid concentration. The solubility limitations lead to the use of inefficient slurry conditions or to the need for large volumes of solution to oxidize small quantities of the organic compound. Similar problems are encountered with other salts of low solubility.

European Patent Application No. 0075828 of Mayeda et al describes a process for oxidizing fused ring compounds to their respective quinones using ceric nitrate in dilute nitric acid. Although solubility does not present a problem, the nitrate anion is known to react with the organic reactant forming nitrogen containing by-products which are difficult to handle and remove. Cerium salt solutions containing perchlorate anions have also been disclosed as a useful oxidant [Prospects for the Indirect Electrolytic Oxidation of Organics, by N. Ibl et al., AIChE Symposium Series, Electroorganic Synthesis Technology, Pg. 45, (1979)] but it is well known that the perchlorate reacts explosively with organic materials and, therefore, is unsuitable for commercial scale processes.

M. Marrocco et al [J. Org. Chem., Vol. 48, No. 9, Pg. 1487 (1983)] conducted a study of the oxidation of an organic substrate by various cerium salts in different acid electrolytes. Each of the cerium salt systems contained excess perchlorate or trifluoroacetate anions and the cerium ions were maintained at very low concentrations. Even at the low concentrations the systems were, in some instances, slurries. Of the systems examined, the cerium salt of trifluoroacetate in trifluoroacetic acid proved most effective although conversion and selectivity were still low. Several systems, including cerium perchlorate or trifluoroacetate in methanesulfonic acid, were shown to be ineffective.

The oxidation of naphthalene to naphthaquinone using an aqueous solution containing acetonitrile was reported by M. Periasamy et al, in Synthesis, Pg. 330 (1977). The process required the use of ceric ammonium sulfate in 4 normal sulfuric acid and acetonitrile. Although high yields were achieved, the system exhibited very low rates of reaction. The process required extended reaction time (6 hours) and isolation of the product was difficult due to the precipitation of the cerous salt out of solution as the oxidation proceeded.

The oxidation of aromatic and alkyl substituted aromatic compounds with ceric methanesulfonate is disclosed in applicant's copending application, U.S. Ser. No. 859,548 filed May 5, 1986, now U.S. Pat. No. 4,639,298. The process requires the use of an aqueous solution which maintains a high concentration of free methanesulfonic acid. This high acidity requirement has been found to inhibit formation of certain desired products.

It must be understood that although cerous/ceric ions have been known and used in oxidation reactions, there is a need to have a system wherein the ceric oxidant can be sufficiently stable under oxidizing conditions to be useful in indirect electrochemical processes, to be capable of undergoing repeated cycling between its cerous ($Ce^{+3}$) and ceric ($Ce^{+4}$) species in a high degree of efficiency under the reaction and electrolysis conditions, to be highly selective in forming the desired carbonyl group containing compounds, to be capable of exhibiting high reaction rates to make the process attractive on a commercial scale, to have high solubility of the cerous specie to aid in the efficiency of ceric regeneration and to provide an easy means for separation and recovery of the organic product. It is readily seen that a means of achieving this combination of desired properties would aid in providing a process which would find a high degree of acceptance in electrochemical oxidation of aromatic and alkyl substituted aromatic compounds.

SUMMARY OF THE INVENTION

The present invention is directed to an electrochemical process wherein ceric ions are generated and used as an oxidant to transform aromatic and alkyl substituted aromatic compounds to carbonyl containing compounds in good selectivity. The present process requires the utilization of at least 0.2 molar concentration of cerium salts of methanesulfonic acid dissolved in an aqueous system containing an organic cosolvent which exhibits at least 2% solubility in water and is substantially inert under the reaction conditions. The system may contain low concentrations of the free methanesulfonic acid. The cerium salt solution, as described hereinbelow, exhibits the desired combination of properties (stability, solubility, reactivity, capability to achieve high current density, capability of repeated cycling between cerous and ceric, and selectivity of product formation) to provide a commercially attractive process.

DETAILED DESCRIPTION OF THE INVENTION

The present invention is directed to a process for selectively forming carbonyl containing compounds from respective aromatic compounds.

Certain terms used in the present specification and in the appended claims are defined herein below to aid in providing a clear description of the invention:

The term "aromatic" shall, unless specifically indicated otherwise, refer to benzylic and fused benzylic compounds such as benzene, naphthalene, anthracene and the like. The compounds may be unsubstituted or may contain substitution groups which are inert to oxidation such as halides, alkoxy, nitro, sulfonyl, amide, tertiary amino, tertiary alkyl and carboxylate groups.

The term "alkyl aromatic" refers to $C_1$-$C_6$ alkyl substituted benzylic and fused benzylic compounds. The compounds shall contain one or more than one primary or secondary $C_1$-$C_6$ alkyl group attached to the aromatic ring and may, in addition, contain groups which are inert to oxidation such as halides, alkoxy, nitro, sulfonyl, amido, tertiary amino, tertiary alkyl, and carboxylate ester groups. Examples of such compounds include toluene, (o, m or p) xylene, trimethylbenzene, (o, m or p) ethyltoluene, (o, m or p) propyltoluene, (o, m or p) methoxyethylbenzene, (o, m or p) ethoxyethylbenzene, 1, 2 dimethylnaphthalene, (o, m or p) methyl-N,N-dimethylaniline (o,m or p) chlorotoluene and the like.

The term "indirect electrochemical oxidation" refers to an oxidation of an aromatic or alkyl aromatic compound which proceeds in two steps such that the first step provides a metal ion oxidant (e.g. $Ce^{+4}$) by anodic charge exchange and the second step comprises the reacting of the metal ion oxidant with an aromatic or alkyl aromatic compound to produce carbonyl containing compounds. The oxidation of the aromatic or alkyl aromatic compound does not occur selectively in the absence of the metal ion oxidant. The indirect electrochemical oxidation of the organic substrate can be conducted in the electrochemical reactor (in-cell) or in a separate reactor (ex-cell).

The terms "cerous", "ceric" and "cerium" refer, respectively to the cerium ion or salt of a cerium ion in its lower valence state (+3), its higher valence state (+4) and as a mixture of both lower and higher valence state species.

The term "system" refers to the water and organic cosolvents. The organic cosolvent must have at least 2 percent solubility in water at the process conditions.

The present invention provides an improved indirect electrochemical oxidation process. The improvement requires the utilization of an aqueous system having at least 0.2 molarity of cerium salts of methanesulfonic acid dissolved in the system. The system may contain from 0 up to about 1.3 molar concentration of free methanesulfonic acid. The present invention provides efficient reaction rates and high selectivity for oxidizing the organic substrate and high current efficiency to regenerate the oxidant.

In copending application, U.S. Ser. No. 859,548, it was disclosed that both the cerous and ceric methanesulfonate salts exhibit good solubility when the solution contains at least 1.5 molar concentration of free methanesulfonic acid in the aqueous medium. At low concentrations of free methanesulfonic acid, the solubility of the cerium(IV) salt decreases markedly. The use of cerium(IV) methanesulfonate slurries at low acid concentration has been associated with low reaction rates and poor selectivity to the carbonyl derivative of the aromatic and alkyl aromatic substrate.

It has now been unexpectedly found that cerium(IV) methanesulfonates can be used as an effective oxidant for indirect electrochemical synthesis at low concentrations (0 to about 1.3 molar) of free methanesulfonic acid when used according to the present invention which requires the presence of an organic cosolvent and the combined cerium ion concentration to be at least 0.2 molar. The utilization of the presently required system unexpectedly provides the combination of advantages of:

(1) fast reaction rate of the ceric oxidant with the organic reactant;
(2) high selectivity of the oxidation of the organic reactant to formation of desired carbonyl containing compounds;
(3) high solubility of the cerous ions;
(4) high current efficiency at high current density (of at least about 75 mA/cm$^2$ or greater) to provide effective anodic oxidation of the cerous ions to ceric ions.

The subject process requires the use of the salts of cerium methanesulfonate. Solutions of the salts can be readily formed by reacting a cerous salt of an inorganic acid with aqueous methanesulfonic acid. The resulting aqueous solution should be substantially free of extraneous anions of other acids such as sulfates, nitrate, perchlorate, halide, acetate, trifluoroacetate and the like. It is preferred that the concentration of such extraneous anions be maintained at a low value of from 0 to 0.5, preferably from 0 to 0.1 mole per mole of cerium ions present in the solution. It is therefore most desired to form the subject salts from cerous carbonate, cerium dioxide, cerium hydroxide and the like and most preferably from cerous carbonate. When other inorganic acid salts are used, their anions should be substantially removed from the solution by known means prior to using solution in the subject process. For example, if sulfate ions are present they can be removed by precipitation with lead(II) carbonate. Similarly, chloride ions can be removed by treating the solution with silver carbonate. Other extraneous ions can be removed in similar manners known in the art.

The cerous salt of methansulfonic acid can be dissolved in the presently described system at high concentrations without causing precipitation. Cerium concentrations, in the initial system, should be at least 0.2 molar, with at least 0.5 molar being preferred. Cerium concentrations of 1 molar and greater in solution can be achieved using the present aqueous-organic cosolvent system which contain low concentrations of from 0 to about 1.3 molar of free methanesulfonic acid in excess of that needed to form cerous methanesulfonate salt which is present in the electrolytic solution. Although the cerium(IV) salt is substantially insoluble in the system at the low acid concentration, it has been unexpectedly found that the organic reactant is capable of being rapidly oxidized by the ceric specie present in the system. The total concentration of cerium present in the system (dissolved and dispersed) should be at least 0.2 molar with higher concentrations of at least 0.5 being preferred and at least 1 molar being most preferred. The specific concentration which meets economic, process and solubility restraints can be readily determined by conventional technique.

The organic cosolvent of the present system must have a solubility with water which is at least 2 percent (on a weight-to-weight basis) and preferably at least 5 percent. The organic cosolvent must be substantially inert under the conditions encountered in the present process. The cosolvent must, therefore, be substantially inert with respect to the acidic and redox conditions of the process. Compounds which are most suitable as the organic cosolvent include nitriles such as acetonitrile, propionitrile, butyronitrile and the like; nitroalkanes such as nitromethane and nitroethane; alkoxy compounds such as dimethyl ether, diethyl ether, methylene dimethyl ether, methylene diethyl ether, tetrahydrofuran, 1,2-dimethoxy ethane and the like; sulfonyl containing compounds such as dimethyl sulfone, tetramethyl sulfone (sulfolane), diethyl sulfone and the like; sulfoxides, such as dimethyl sulfoxide and the like; amides such as N-methyl pyrrolidone, dimethylformamide, 2-pyrrolidone and the like; organic carbonates, such as propylene carbonate and the like; alcohols such as methanol, ethanol, t-butanol and the like; ketones such as acetone, methyl ethyl ketone and the like; their equivalents as well as mixtures thereof. The most preferred organic cosolvents are $C_1$-$C_3$ alkyl nitriles, especially acetonitrile, and $C_1$-$C_2$ nitroalkanes. The organic cosolvent can be present as part of the system in from 2 percent to about 50 percent. It can be introduced into the system as part of the aromatic or alkyl aromatic feed (especially in a batch process) or separately to form the liquid system of the process.

The aqueous system may contain one or a mixture of organic cosolvents. In addition, other conventional materials may be added to the system provided they are inert to the cerium salt and the acid contained therein. Examples of such materials include conventional anionic, cationic or nonionic surfactants.

The cerium(IV) species may be generated by electrolysis and has been found to be a good one electron oxidant which can rapidly and effectively oxidize aromatic and alkyl aromatic compounds to their respective carbonyl compounds in high yield and selectivity. The present process accomplishes this desired result even though the cerium(IV) specie is a solid dispersed in the system. The process may be carried out as a single chemical oxidation or as a mediated electrochemical process. The mediated process is preferred as it permits the use and reuse of the cerium methanesulfonate.

The generation and subsequent regeneration of ceric oxidant can be readily carried out by supplying the system containing the cerium methanesulfonate to an electrolytic cell in either a batch or continuous manner. The cell may be either undivided or divided by a porous partition wall or membrane between electrodes. The electrodes may be of any suitable form such as plates, lattices, expanded metal, or reticulated porous material and the like. The anode may be any of the known materials suitable for preforming the metal-ion oxidation and are, preferably selected from lead, lead oxide, platinum, platinized titanium, platinized niobium or metal oxide-titanium composite. The cathode of the cell may be any of the known materials suitable for performing reductions in the aqueous-acid solutions with or without the presence of metal ions such as, for example, steel, copper, and nickel. The use of the presently described cerium salt containing system has, as one of its unexpected properties, the ability to readily and effectively generate and regenerate ceric oxidant from cerous ions at high current density. Another unexpected property is the ability of the solution to cause a clean cathodic reduction without production of by-products which detract from the process and require separation therefrom. The electrolysis can be performed at voltages ranging from about 2 to 20 volts with current density ranging between about 0.1 to about 500 mA/cm$^2$, preferably from 10 to 400 mA/cm$^2$ and most preferably from 30 to 300 mA/cm$^2$ (based on electrode area excluding roughness factor). The electrolysis may be conducted at a temperature of from about −20° to 150° C. and preferably from 0° to 100° C. It is most preferable to have the cell temperature and the reaction temperature (where the cell and chemical reactor are separate) be substantially the same.

The organic substrates which can be effectively oxidized using the solution of the present process are aromatic and alkyl aromatic compounds. The aromatic compounds include benzylic and fused benzylic ring compounds which may be unsubstituted or be substituted with a group which is substantially inert to oxidation. Examples of such compounds include benzene, naphthalene, anthracene and the like as well as such compounds which contain groups attached to the ring which are inert to the present indirect oxidation. Such groups can be readily determined by simple laboratory testing and include ($C_1$–$C_4$) alkoxy, tert-alkyl ($C_4$–$C_7$), phenoxy, nitro, tertiary amino, sulfonyl, amido, and carboxylic groups and the like. The alkyl substituted aromatic compounds include the above defined aromatic compounds which further contains at least one primary alkyl or secondary alkyl group or both.

The organic substrates described above are oxidized to their respective carbonyl containing compounds by contacting the organic compound with the weakly acidic aqueous system described above which contains the oxidant, ceric methanesulfonate. The contacting of the oxidant and the organic compound may be conducted directly within the electrolytic cell. However, it is preferable to transfer the subject oxidant containing solution to a separate reactor vessel where it is contacted with the organic compound to be oxidized under agitation. The organic compound can be introduced to the reactor either dissolved or dispersed in the aqueous phase or dissolved in an organic liquid. The organic substrate can be present in from about one half to twice the stoichiometric equivalent of the oxidant present. Lesser or greater amounts can be used without adverse effect. In certain instances, large (3 to 10 times) excess of substrate (in particular, alkylaromatic) may be used to enhance the reaction.

It has been unexpectedly found that the system used in the present process is capable of providing ceric ions which exhibit high reaction rate in oxidizing the aromatic and alkyl aromatic compounds and to have high solubility of the spent cerium(III) material which permits easy separation and recovery of the oxidized product. In addition, the subject process unexpectedly provides a means for readily and selectively forming quinones (from aromatic compounds) and aldehydes or ketones (from alkyl aromatics) without substantial by-product formation.

The organic oxidation can be carried out under ambient temperature and pressure conditions. The temperature may be varied from about 0° to about 100° C. with from 20° to 75° C. being preferred. The pressure may be elevated or reduced for process reasons.

The system removed from the reaction zone contains product and spent metal ion oxidant (cerous). The product can be readily separated from the system by phase-separation, distillation, precipitation or extraction with an appropriate solvent such as alkanes, acyclic or cyclic haloalkanes such as chloroalkanes and the like. The particular mode of separation will depend upon the identity of the product formed and can be readily ascertained by the artisan.

The resultant system (after separation of the product) will contain cerous salt as the sole or major component and may contain small amounts of unreacted ceric salt. This system can be returned to the electrolytic cell for regeneration of the ceric ion oxidant. It has been found that the ceric/cerous salts used herein undergo a multiplicity of cycles without formation of by-products which have detrimental effect on the efficiency of the process.

The following examples are given for illustrative purposes only and are not meant to be a limitation on the present invention as defined by the claims appended hereto. All parts and percentages are by weight unless otherwise indicated.

EXAMPLE I 94 parts of methanesulfonic acid was added slowly to a stirred suspension of 61 parts of cerium(III) carbonate (obtained as pentahydrate) in 60 parts water. Upon completion of carbon dioxide evolution, additional water was added to make the total volume 150 ml. 20 parts by volume of acetonitrile was added and the resultant system was introduced into the anolyte compartment of a plate and frame type electrolytic cell. The anode was a flat sheet (ca. 50 cm$^2$) ruthenium oxide-titanium oxide composite on titanium. The anolyte compartment was separated from the catholyte compartment by a commercial perfluorinated ion exchange membrane (Nafion 390). The anolyte temperature was ca 40° C. and a constant current of 5 amps was passed for 30 minutes resulting in a Ce(IV) concentration of 0.37 M and a current efficiency of 67%. The catholyte compartment contained a stainless steel cathode and caused a clean proton reduction to hydrogen gas.

EXAMPLE II 100 parts by volume of 0.6 M Ce(IV) methanesulfonate (a slurry) and 0.8 M $CH_3SO_3H$ in water was purged with nitrogen, and then 1.28 parts of naphthalene in 30 parts by volume of 1,2-dichloroethane was added. The mixture was stirred vigorously in a 60° oil bath, and 30 parts by volume of acetonitrile was added. The reaction was complete in about 10 min. The resulting mixture was cooled and extracted with 300 parts methylene chloride. Quantitative analysis by gas chromatography showed 0.08 parts naphthalene and 1.44 parts 1,4-naphthoquinone (91.4% yield, 97.2% selectivity).

EXAMPLE III

This example is given for comparative purposes only. The procedure of Example II was repeated except that acetonitrile was not added. The solid Ce(IV) material was not consumed until 60 minutes, at which time the mixture was analyzed as in Example II and found to contain 0.25 parts naphthalene and 1.07 parts naphthoquinone (67.6% yield, 83.9% selectivity) and 0.05 parts phthalic acid (2.8% yield, 2.9% selectivity). This example shows that the reaction time was about six times as long and formed the desired quinone product in a yield which was substantially lower than achieved in Example II.

EXAMPLE IV

The procedure of example III was repeated except that 40 parts by volume of nitromethane was used in place of the 1,2-dichloroethane. The reaction was complete in 15 minutes resulting in 83% yield, 94% selectivity to 1,4-naphthoquinone, based on naphthalene.

EXAMPLE V 100 parts by volume of 0.4 M Ce(IV) methanesulfonate (a slurry) and 1.0 M $CH_3SO_3H$ in water was purged with nitrogen and then 1.45 parts of p-methylanisole in 30 parts by volume of 1,2-dichloroethane was added. The mixture was stirred vigorously at 25° C., and 80 parts by volume of acetonitrile was added. After 60 minutes, the mixture was extracted with 300 parts of methylene chloride. Quantitative analysis by gas chromatography showed 0.23 part p-methylanisole and 0.96 part p-anisaldehyde (59% yield, 70% selectivity).

For comparative purposes, the above procedure was repeated except that acetonitrile was not added. Quantitative analysis of the products by gas chromatography showed the overall yield and the selectivity to be reduced 48 percent yield and 56 percent selectivity.

What is claimed:

1. A process for forming carbonyl group containing compounds from their respective organic substrates selected from aromatic and alkyl substituted aromatic compounds comprising contacting the organic substrate with ceric methanesulfonate in an aqueous system composed of water and organic cosolvents containing from 0 to about 1.3 molar concentration of free methanesulfonic acid and having at least 0.2 molar cerium concentration; said organic cosolvent being substantially inert with respect to the ceric methanesulfonate and free methanesulfonic acid and soluble in water in at least 2 weight percent.

2. The process of claim 1 wherein the free acid concentration is from 0 to about 1 molar.

3. The process of claim 1 wherein the aqueous system has a concentration of extraneous anions in from 0 to about 0.5 mole/mole of cerium ions.

4. The process of claim 1 wherein the aqueous system contains a surfactant.

5. The process of claim 1 wherein the organic cosolvent is selected from a $C_1$-$C_3$ alkyl nitrile and mixtures thereof.

6. The process of claim 2 wherein the organic cosolvent is selected from a $C_1$-$C_3$ alkyl nitrile and mixtures thereof.

7. The process of claim 3 wherein the organic cosolvent is selected from a $C_1$-$C_3$ alkyl nitrile and mixtures thereof.

8. The process of claim 5 wherein the organic cosolvent is selected from acetonitrile.

9. The process of claim 6 wherein the organic cosolvent is selected from acetonitrile.

10. The process of claim 7 wherein the organic cosolvent is selected from acetonitrile.

11. The process of claim 1 wherein the organic cosolvent is selected from a $C_1$-$C_2$ nitroalkane or mixtures thereof.

12. The process of claim 2 wherein the organic cosolvent is selected from a $C_1$-$C_2$ nitroalkane or mixtures thereof.

13. The process of claim 3 wherein the organic cosolvent is selected from a $C_1$-$C_2$ nitroalkane or mixtures thereof.

14. The process of claim 8 wherein the cerium concentration is at least 0.5 molar.

15. The process of claim 9 wherein the cerium concentration is at least 0.5 molar.

16. The process of claim 10 wherein the cerium concentration is at least 0.5 molar.

17. The process of claim 1 wherein the organic substrate is present in from about 3 to 10 times stoichiometric excess with respect to the Ce(IV) concentration.

18. An indirect electrochemical oxidation process to oxidize aromatic and alkyl substituted aromatic compounds comprising
   (a) contacting the organic substrate with ceric methanesulfonate in an aqueous system composed of water and organic cosolvents containing from 0 to about 1.3 molar concentration of free methanesulfonic acid and having at least 0.2 molar cerium concentration; said organic cosolvent being substantially inert with respect to the ceric methanesulfonate and free methanesulfonic acid and soluble in water in at least 2 weight percent;
   (b) separating and recovering the carbonyl containing product from the system to yield a spent system rich in cerous salts;
   (c) transferring the spent system to an electrochemical cell to cause regeneration of a system rich in the ceric salt; and
   (d) repeating steps (a), (b) and (c).

19. The process of claim 18 wherein step (a) is conducted at a temperature of from about 0° C. to 100° C. and the electrolysis of step (c) is conducted at a cell voltage ranging from about 2 to 20 volts with a current density of from 10 to 400 $mA/cm^2$.

20. The process of claim 18 wherein the solution has a concentration of extraneous anions of from 0 to about 0.5 mole per mole of cerium ions present.

21. The process of claim 19 wherein the solution has a concentration of extraneous anions of from 0 to about 0.5 mole per mole of cerium ions present.

22. The process of claim 18 wherein the organic substrate is introduced as a solution in an organic solvent.

23. The process of claim 18 wherein the aqueous system contains a surfactant.

24. The process of claim 18 wherein the oxidation of the aromatic or alkyl aromatic compound is performed in the electrochemical cell.

25. The process of claim 18 wherein the system contains an alkyl aromatic compound in from about three to about 10 times the stoichiometric equivalence of the cerium present.

26. The process of claim 18 wherein the organic cosolvent is selected from a $C_1$-$C_3$ alkyl nitrile and mixtures thereof.

27. The process of claim 19 wherein the organic cosolvent is selected from a $C_1$-$C_3$ alkyl nitrile and mixtures thereof.

28. The process of claim 20 wherein the organic cosolvent is selected from a $C_1$-$C_3$ alkyl nitrile and mixtures thereof.

29. The process of claim 21 wherein the organic cosolvent is selected from a $C_1$-$C_3$ alkyl nitrile and mixtures thereof.

30. The process of claim 26 wherein the organic cosolvent is selected from acetonitrile.

31. The process of claim 27 wherein the organic cosolvent is selected from acetonitrile.

32. The process of claim 28 wherein the organic cosolvent is selected from acetonitrile.

33. The process of claim 29 wherein the organic cosolvent is selected from acetonitrile.

* * * * *